US010111701B2

(12) United States Patent
Shahlaie et al.

(10) Patent No.: US 10,111,701 B2
(45) Date of Patent: Oct. 30, 2018

(54) MICRO-BIPOLAR ENDOSCOPIC ENDONASAL CAUTERY DEVICE

(71) Applicant: THE REGENTS OF THE UNIVERSITY OF CALIFORNIA, Oakland, CA (US)

(72) Inventors: Kiarash Shahlaie, Sacramento, CA (US); Elizabeth Lim, Shoreview, MN (US); Jonathan Oakden, Sacramento, CA (US); Paul Riemenschneider, Ukiah, CA (US); Travis Schraeder, Elk Grove, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 931 days.

(21) Appl. No.: 14/549,816

(22) Filed: Nov. 21, 2014

(65) Prior Publication Data

US 2015/0148801 A1    May 28, 2015

Related U.S. Application Data

(63) Continuation of application No. PCT/US2013/044802, filed on Jun. 7, 2013.
(Continued)

(51) Int. Cl.
*A61B 18/14* (2006.01)
*A61B 18/00* (2006.01)
(Continued)

(52) U.S. Cl.
CPC .. *A61B 18/1445* (2013.01); *A61B 2017/2936* (2013.01); *A61B 2017/2944* (2013.01);
(Continued)

(58) Field of Classification Search
CPC .............. A61B 18/085; A61B 18/1442; A61B 18/1445; A61B 18/1447;
(Continued)

(56) References Cited

U.S. PATENT DOCUMENTS 5,454,378 A    10/1995  Palmer et al.
5,893,873 A     4/1999  Rader et al.
(Continued)

OTHER PUBLICATIONS

Korean Intellectual Property Office (KIPO), International Search Report and Written Opinion dated Sep. 13, 2013, related PCT International Application No. PCT/US2013/044802, pp. 1-10, with claims searched, pp. 11-17.

*Primary Examiner* — Thomas Giuliani
(74) *Attorney, Agent, or Firm* — O'Banion & Ritchey LLP; John P. O'Banion

(57) ABSTRACT

A bipolar electrosurgical forceps device having a handle at the proximal end and forceps jaws at the distal end is described. These two ends are connected via an elongated tubular section that houses the actuating member for controlling the motion of the forceps at the distal end relative to the motion of the proximal handle. A dovetail member connects the forceps to a shaft that is slidably disposed in the tubular section at the distal end of the device, where the tubular section constrains the motion of the two jaws perpendicular relative to the axial direction. A coupling member is attached to the actuating member where drive slots interact with the drive pins on the forceps, whereby squeezing the handle causes the desired relative parallel opening or closing motion of the forceps jaws.

20 Claims, 6 Drawing Sheets

Related U.S. Application Data

(60) Provisional application No. 61/781,003, filed on Mar. 14, 2013, provisional application No. 61/656,938, filed on Jun. 7, 2012.

(51) Int. Cl.
 *A61B 17/29* (2006.01)
 *A61B 17/32* (2006.01)

(52) U.S. Cl.
 CPC ............... *A61B 2017/2945* (2013.01); *A61B 2017/320044* (2013.01); *A61B 2018/00327* (2013.01); *A61B 2018/00595* (2013.01)

(58) Field of Classification Search
 CPC .... A61B 2017/2913; A61B 2017/2916; A61B 2017/2933; A61B 2017/2936; A61B 2017/2944; A61B 2018/1462; A61B 2018/145; A61B 2018/00595; A61B 2018/0063
 USPC ............... 606/41, 50–52, 205, 207, 210, 211
 See application file for complete search history.

(56) References Cited

U.S. PATENT DOCUMENTS

| | | | |
|---|---|---|---|
| 7,758,573 B2 | 7/2010 | Comori et al. | |
| 2002/0099375 A1 | 7/2002 | Hess et al. | |
| 2006/0271042 A1* | 11/2006 | Latterell | A61B 18/1445 606/51 |
| 2007/0106297 A1* | 5/2007 | Dumbauld | A61B 18/1445 606/51 |
| 2008/0208193 A1* | 8/2008 | Yamatani | A61B 18/1482 606/48 |
| 2011/0046439 A1* | 2/2011 | Pamnani | A61B 1/018 600/104 |
| 2011/0251612 A1* | 10/2011 | Faller | A61B 18/1445 606/52 |

\* cited by examiner

MICRO-BIPOLAR ENDOSCOPIC ENDONASAL CAUTERY DEVICE

CROSS-REFERENCE TO RELATED APPLICATIONS

This application is a 35 U.S.C. § 111(a) continuation of PCT international application number PCT/US2013/044802 filed on Jun. 7, 2013, incorporated herein by reference in its entirety, which claims priority to, and the benefit of, U.S. provisional patent application Ser. No. 61/781,003 filed on Mar. 14, 2013, incorporated herein by reference in its entirety, and U.S. provisional patent application Ser. No. 61/656,938 filed on Jun. 7, 2012, incorporated herein by reference in its entirety. Priority is claimed to each of the foregoing applications.

The above-referenced PCT international application was published as PCT International Publication No. WO 2013/185086 on Dec. 12, 2013, which publication is incorporated herein by reference in its entirety.

STATEMENT REGARDING FEDERALLY SPONSORED RESEARCH OR DEVELOPMENT

Not Applicable

INCORPORATION-BY-REFERENCE OF MATERIAL SUBMITTED IN A COMPUTER PROGRAM APPENDIX

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. § 1.14.

BACKGROUND

1. Technical Field

The present disclosure relates generally to endoscopic surgical devices, and more particularly to bipolar electrosurgical devices for coagulation, cutting and micro-dissection of tissue.

2. Background Discussion

Neurosurgery is the surgical specialty that deals with the nervous system, generally the brain, spinal cord, and peripheral nerves. Surgery may be required in these regions due to tumors, traumatic injury, birth defects, cancer, aneurysms, and other complications. Depending on the condition and location within the body, different techniques are used to access the target region. In the 1980's, minimally invasive surgery techniques were pioneered and developed, and have since changed the standards for how many operations are performed. One of the largest benefits of minimally invasive surgery is that the patient experiences less operative trauma compared to an equivalent invasive procedure. Other benefits include less scaring, less blood loss, less risk of infection, faster recovery, and shorter hospital stay.

In the past, the base of the skull was one of the most challenging anatomic regions to access. In order to operate in this region, facial disarticulations and removal of the facial skeletons were necessary. Layers of bony, vascular, and neural structures were removed from the patient until the surgeons reached the target region, usually deep within the brain. This outside-in approach is very traumatic for the patient and the risk for impairing normal functions is extremely high.

In recent years, the use of minimally invasive techniques and devices has been applied to access the skull base region. This surgical technique is called the Endoscopic Endonasal Approach (EEA), and is used to remove tumors and lesions of the skull base and the top of the spine by directly operating through the nose and sinuses. Long, thin, highly sophisticated instruments are used to perform these surgeries. This inside-out approach using EEA eliminates the need to remove critical facial structures to reach tumors near the base of the brain.

One of the main concerns during surgical procedures is minimizing blood loss. One technique used to reduce or stop bleeding from small vessels in neurosurgical procedures is electrocautery. Electrocautery is the process of burning or destroying tissue using a metal probe heated by electric current. There are two types of electrocautery devices: monopolar and bipolar. Bipolar devices can better control and direct the electric field generated compared to monopolar devices, thus resulting in less adjacent tissue damage.

The currently available endoscopic bipolar electrosurgical devices lack certain functionality and precision that are desired for endoscopic surgical procedures. Most of the currently available endoscopic bipolar electrosurgical devices employ tweezers style forceps jaws with the use of a tubular body to force the jaws closed and rely on the natural spring restoring force of the tweezers to open the jaws. The first issue that arises from this design choice is that the closing point location of the forceps is not fixed axially. This complicates the perception and actuation of the closing point and can lead to the surgeon missing their intended target. The severity of this issue is amplified especially for neurosurgical procedures due to the high risk of damaging life critical adjacent tissue structures. The second issue that arises from the tweezers type design is that the device cannot reliably perform precise and controlled micro-dissection. Micro-dissection is the procedure surgeons use with the opening motion of the forceps to spread tissue apart in a controlled manner.

BRIEF SUMMARY

The technology described herein generally comprises a bipolar electrosurgical forceps device having a handle at the proximal end and forceps jaws at the distal end. These two ends are connected via an elongated tubular section that houses the actuating member for controlling the motion of the forceps at the distal end relative to the motion of the proximal handle. A dovetail coupling member connects the forceps to the tubular section at the distal end and constrains the motion of the two jaws perpendicular relative to the axial direction. An actuating member is slidably received within the dovetail coupling, where drive slots on the actuating member interact with the drive pins on the forceps, whereby squeezing the handle causes the desired relative parallel opening or closing motion of the forceps jaws.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology of this disclosure will be more fully understood by reference to the following drawings which are for illustrative purposes only:

DETAILED DESCRIPTION

The description below with respect to FIG. 1 through FIG. 13 details bipolar electrosurgical forceps devices comprising various configurations of a handle at the proximal end and forceps jaws at the distal end. It is appreciated that the sub-assemblies and specific component parts may be used interchangeably with each other, where appropriate.

Figure 1:
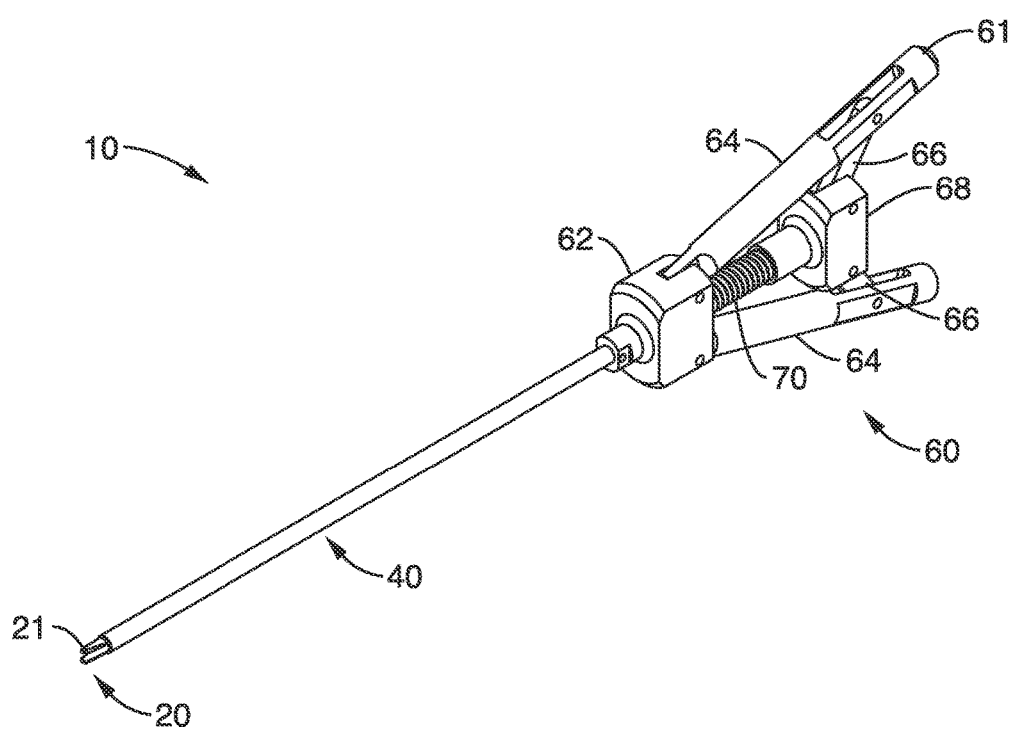
FIG. 1 is a perspective view of an assembled micro-endoscopic cautery device of the technology described herein having a tweezers-style handle in an open configuration.

FIG. 1 is a perspective view of an assembled micro-endoscopic cautery device 10 of the technology described herein having a tweezers-style handle 60 in an open configuration at proximal end 61. The distal end 21 of the device 10 comprises a forceps tip sub-assembly 20 configured for precise and controlled gripping, cautery, and/or micro-dissection of tissues.

As used herein, the term "proximal" refers to the end of the device closest to the user, the term "distal" refers to the end of the device farthest away from the user, the term "axial" refers to the longitudinal axis of the device, and the term "tip" refers interchangeably with the term distal end forceps jaw. The terms herein otherwise have their ordinary meanings.

The distal forceps tip sub-assembly 20 and proximal handle sub-assembly 60 are connected via an elongated axial motion sub-assembly 40, and an elongated tubular section 88 that houses the actuating components for controlling the motion of the forceps 20 at the distal end 21 relative to the motion of the proximal handle 60.

In a preferred embodiment, FIG. 1 shows an embodiment of a bipolar electrosurgical forceps device 10 according to the technology described herein. Much of the tip sub-assembly 20 (shown greater detail in FIG. 2) is hidden inside the outer tube 88, with exception of portion of the forceps jaws or tips 12a and 12b, which are shown protruding out of the distal end of the outer tube 88 (see also FIG. 2).

Figure 2:
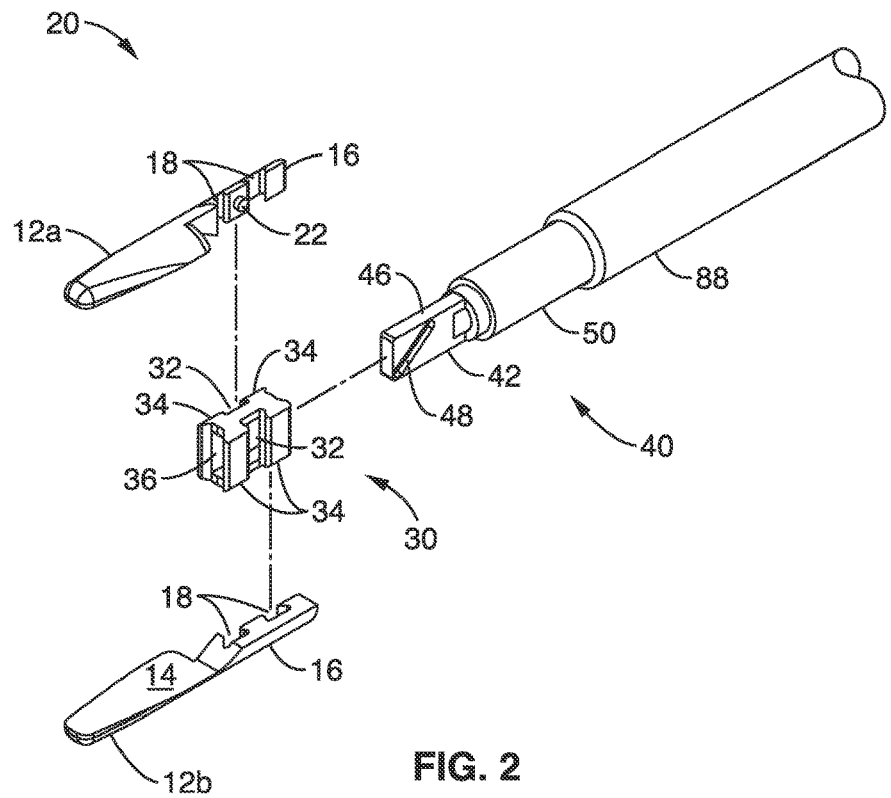
FIG. 2 is an exploded perspective view of the tip sub-assembly and distal end of the device of FIG. 1.

FIG. 2 shows an exploded perspective view of the tip sub-assembly 20, distal end of axial motion sub-assembly 40 and device 10. The tip sub-assembly 20 comprises two distal forceps jaws or tips 12a and 12b and a dovetail backbone or tip coupling member 30 that is configured to slidably mate with a slide or actuating member 42 in the axial direction and the tips 12a and 12b in an orthogonal direction. The forceps jaws or tips 12a and 12b each have a flat planar gripping surface 14 that are generally configured to be parallel to each other throughout activation of the forceps assembly 20, which via constraint from the dovetail coupling 30, is substantially isolated to comprise translation in orthogonal to the gripping surfaces 14.

In a closed configuration, the planes 14 of tips 12a and 12b ideally are in contact with each other. It is appreciated that surfaces 14 may comprise non-planar surfaces, e.g. teeth or serrations for gripping, and may also be at a slightly converging angle with each other, such that the distal ends 21 of the tips 12a, 12b have a point contact when closed. The key criteria for the actuation motion of the tips 12a, 12b is that the distal ends 21 remain in the same axial position with respect to each other and the outer sleeve 88 when moving through fully open and fully closed orientations.

As shown in FIG. 2, each of the forceps jaws or tips 12a and 12b have a pair of grooves 18 at their proximal portion 16 that are configured to mate with corresponding tongues 34 and grooves 32 of the backbone coupling 30 to form a dovetail joint. Each of the tips 12a and 12b has a drive pin 22 that is configured to be received in drive slots 48 of the actuating member 42. Drive pin 22 may be a machined protrusion, or a dowel that is press fit into a hole in each tip 12a, 12b. Correspondingly, when the tips 12a and 12b slide onto the dovetail coupling 30, they are constrained by the cooperation of the drive pins 22 and the drive slots 48 on the actuating member 42.

Figure 4:
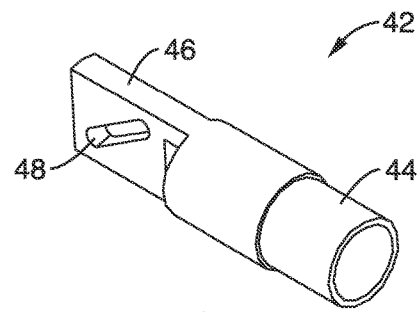
FIG. 4 is a perspective view of the slide transition component of the device of FIG. 1.

The rectangular section 46 of the actuating member 42 (see also FIG. 4 showing a detailed perspective view of the actuating member) is configured to be slidably received in the central aperture 36 of the dovetail coupling 30. When the actuating member 42 is slidably advanced distally and proximally within in the central aperture 36 of the coupling 30, it acts on the drive pins 22 along the drive slots 48 to force a purely vertical motion of the tips 12a and 12b perpendicular to the longitudinal axis of the outer tube 88, i.e. the interface converts axial shaft motion into translation movement of tips 12a and 12b in the orthogonal direction to open and close tips 12a and 12b relative to each other.

Figure 3:
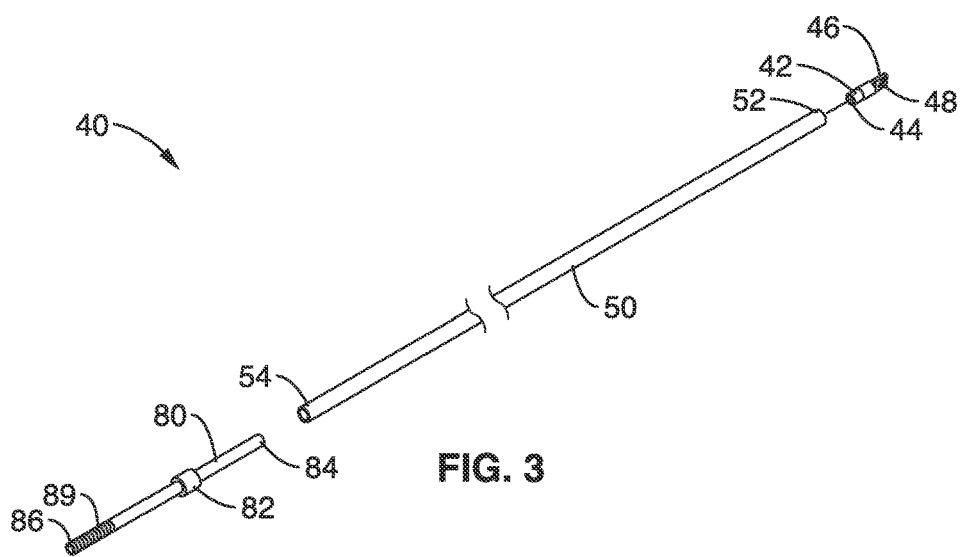
FIG. 3 is an exploded perspective view of the axial-motion sub-assembly of the device of FIG. 1.

FIG. 3 shows an exploded perspective view of the axial motion subsystem 40, which connects the distal tip assembly 20 to the proximal handle, and provides the linear axial actuation to drive the orthogonal opening and closing of the tip assembly 20 from manual manipulation of the proximal handle 20. Proximal section 44 of the actuating member 42 is fixedly attached to the distal end 52 of the inner shaft 50 (e.g. via a press fit tolerance, or by laser welding or adhesive bonding the inner shaft 50 to the proximal section 44). The dovetail coupling 30 is rigidly affixed to the outer tube 88, such as by press fitting, laser welding adhesives, etc.

Referring to FIG. 4, the slots 48 of actuating member 42 are angled at approximately 45 degrees with respect to the longitudinal axis of the inner shaft 50 to provide for smooth vertical translation of the forceps pins 22. The design of the actuating member 42, and particularly the drive slot 48, allows for reversal of the motion of the distal forceps 12a, 12b relative to the proximal handle 60 motion by changing the slot 48 angle. Mirroring the slot 48 angle about the longitudinal axis causes the described reversal.

The proximal end 54 of inner shaft 50 is attached to distal end 84 of handle transition member 80 up to stop 82. The proximal end 86 of the handle transition member 80 is preferably threaded with threads 89 to fixedly attach to the handle assembly 60, as further detailed below with respect to FIG. 5.

It is appreciated that while the actuating member 42, inner shaft 50 and handle transition 80 are preferably separable pieces as shown in FIG. 3 to aid in manufacturing and assembly, the axial motion drive assembly 40, when assembled, operates as one unitary piece. Accordingly, one or more of the actuating member 42, inner shaft 50 and handle transition 80 may be unitary members.

It is appreciated that the sizing of the components in the distal tip assembly and axial motion assembly are configured for micro endoscopic use. For example, an exemplary outer diameter of the outer sheath is approximately 5 mm, and the inner diameter of the inner shaft is approximately 3 mm. The forceps tips 12a and 12b have lengths of approximately 20 mm and widths smaller than the diameter of the inner shaft. It is further appreciated that the above dimensions are for reference purposes only, and that the sizing of individual components may be increased or decreased as per desired use.

Figure 5:
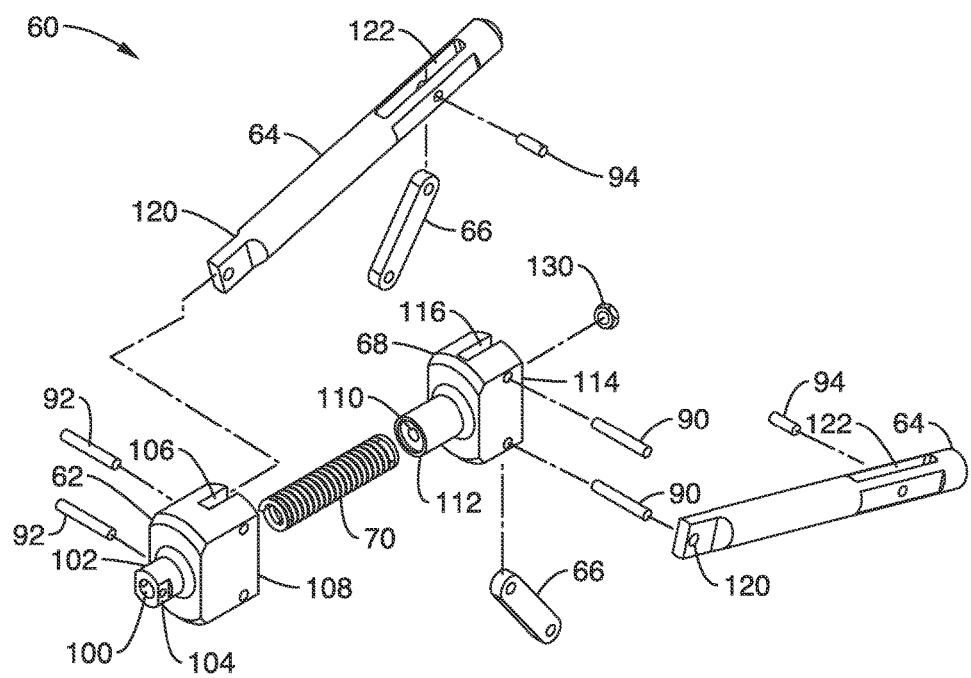
FIG. 5 is an exploded perspective view of the handle sub-assembly of the proximal end of the device of FIG. 1.

Referring now to the exploded perspective view of FIG. 5, as well as back to the perspective assembled view of FIG. 1, the handle sub assembly 60 comprises a main handle body 62, a secondary handle body 68, a pair of opposing handle actuators 64, and a pair of connecting rods 66 that pivotally couple the handle actuators 64 to the secondary handle body 68. Connecting rods 66 are secured within proximal slots 122 of handle actuators 64 with pins 94, and to slots 116 of the secondary handle body 68 via pins 90. The distal ends 120 of the handle actuators 64 are pivotally connected to slots 106 within the main handle body 62 via pins 92. In a preferred embodiment, pins 90, 92 and 94 comprise precision ground dowel pins.

The secondary handle body 68 is connected to the proximal end 86 of the inner shaft 50 via locking nut 130 (which rests against proximal face 114 of the secondary handle body 68) on threaded section 86 of the inner shaft 50 (see FIG. 3). The outer tube 88 is press fit and held within axial aperture 100 of the distal section 102 of the main handle body 62 via setscrews (not shown) in radial aperture 104. The inner shaft 50 is slidably disposed in outer tube 88, axial aperture 100 of main handle body 62, and axial aperture 110 of the secondary handle body 68.

An axial spring 70 is disposed between proximal face 108 of the main handle body 62 and distal section 112 of the secondary handle body 68 to provide a restorative opening action on the handles 64 and corresponding tips 12a and 12b once manual pressure is released on the handles 64.

Figure 6:
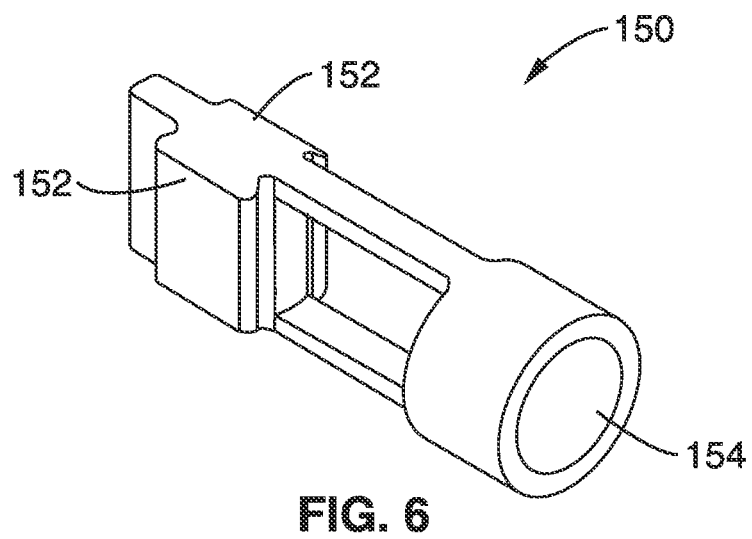
FIG. 6 is a perspective view of an alternative coupling frame component that may be use in conjunction with an alternative assembly to that of the device of FIG. 1.
Figure 7:
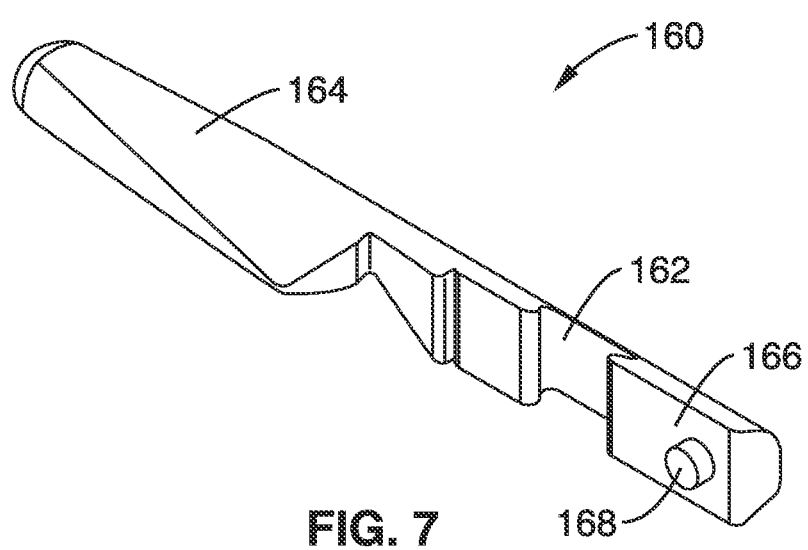
FIG. 7 is a perspective view of an alternative forceps tip component that may be use in conjunction with the frame of FIG. 6.

Referring now to FIG. 6 and FIG. 7, alternative embodiments of a single dovetail backbone or coupling 150 to be used in conjunction with distal forceps tip 160 are illustrated in perspective view. Groove 162 of tip 160 interfaces with tongue 152 on the coupling 150. The coupling 150 has a proximal channel 154 for receiving actuating member 42. The tip 160 also comprises a pin 168 on proximal end 166 for interfacing with slot 48 of the actuating member 42, and a flat gripping surface 164.

It should be noted that the double dovetail configuration of tip assembly 20 shown in FIG. 3 is an enhancement over the single-dovetail configuration shown in FIGS. 6 and 7. To eliminate the bending moment caused by the single dovetail and offset force applied by the pin 168 and actuating member 42, the two dovetail joint configuration of FIG. 3 minimizes binding by distributing the applied pin force between the two dovetail joints. Since this removes the bending moment on the dovetail joint, the binding is eliminated.

It is appreciated that the number of dovetail joints within tip assembly 20 is not limited to only one or two. Rather, the number of dovetail joints can be extended to any desired amount, say three or four. With additional dovetail joints, additional pin and slot movements may be implemented in succession to distribute the load between the numerous pin and slots, as will be described in further detail below with respect to FIG. 9 through FIG. 11.

Figure 8:
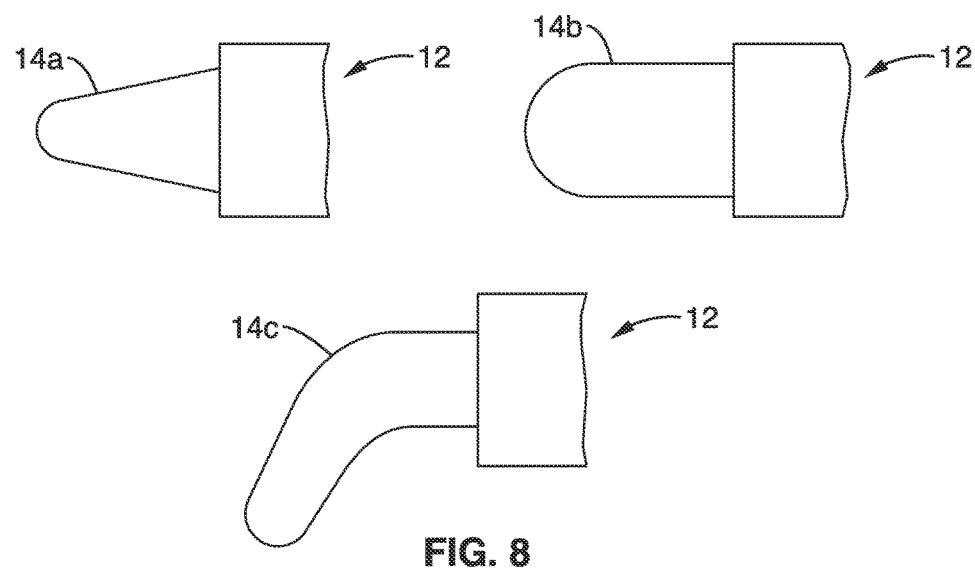
FIG. 8 is a top view illustrating several alternative forceps jaws configurations.

FIG. 8 shows top views of the distal tip 12 to illustrate a few of the possible variations of the tip geometries. Such alternative tip geometries may be selected according to the various uses of this device 10. Possible configurations include a tapered tip shape 14a where the width of the tip decreases towards the distal end, a standard straight tip shape 14b with a rounded distal end, and an angled tip geometry 14c where the tip is bent to one side depending on the view. The angle can be made however desired but the nominal angle is shown at approximately 45 degrees. The tips 12c can be angled left, right, upwards, or downwards. As discussed in further detail below with respect to FIG. 12, a rotation adjustment dial may be included on the proximal handle to allow for control of the orientation of the tips 14a through 14c. This orientation adjustment would consolidate the different tip angle directions to just one tip that can be rotated to any orientation desired.

It is appreciated that the tips 14a through 14c represent only a few of the possible tip geometry formations that are compatible with the device 10 of the technology described herein. Other specialty tip geometry types can also be configured to work with the general device configuration. Furthermore, permutations of multiple tip geometries are also possible, for example, but not limited to, the case of tapering angled tips or straight angled tips.

Figure 9:
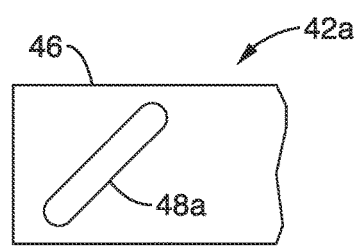
FIG. 9 is a side view of a portion of the coupling member component of the device of FIG. 1.
Figure 10:
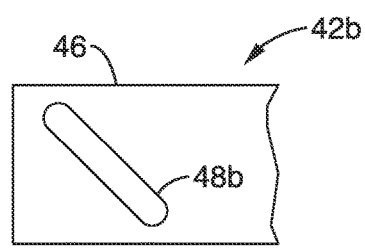
FIG. 10 is a side view of a portion of an alternative coupling member component that may be used with the device of FIG. 1.
Figure 11:
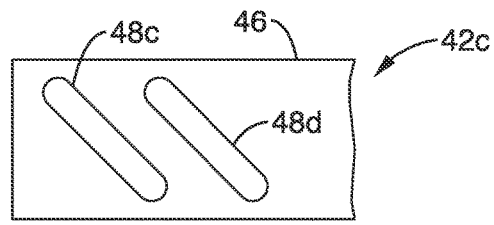
FIG. 11 is a side view of a portion of an alternative coupling member component with a multiple slot configuration that may be used with the device of FIG. 1.

Referring now to FIG. 9 through FIG. 11, the actuating member 42 plays a major role in the functionality of the device 10. The choice of angle and direction of the slot 48 can alter the function of the device 10.

FIGS. 9 and 10, respectively, show how the drive slots 48a and 48b of actuating members 42a and 42b can be mirrored about the longitudinal axis of distal section 46 in order to reverse the relative proximal and distal motions. Depending on the user's preference, the slot orientation will change whether the distal end 20 closes when the proximal end 60 closes, and vice versa. The preferred configuration relates closing of the proximal end 20 to the corresponding closing motion of the distal end 60. The angle (e.g. 45 degrees) of the slot 48*a*, 48*b* will also change the ratio of motion on the proximal end to the length of motion on the distal end.

FIG. 11 depicts the multiple drive slot 48*c*, 48*d* configuration for the actuating member 42*c*. This configuration may be used to distribute the axial force to the forceps jaws 12*a*, 12*b* equally to reduce binding caused by single drive pin configurations. This multiplication of drive slots can be extended to other variant configurations where multiple actuating members are added with corresponding added drive slots to match if desired.

Figure 12:
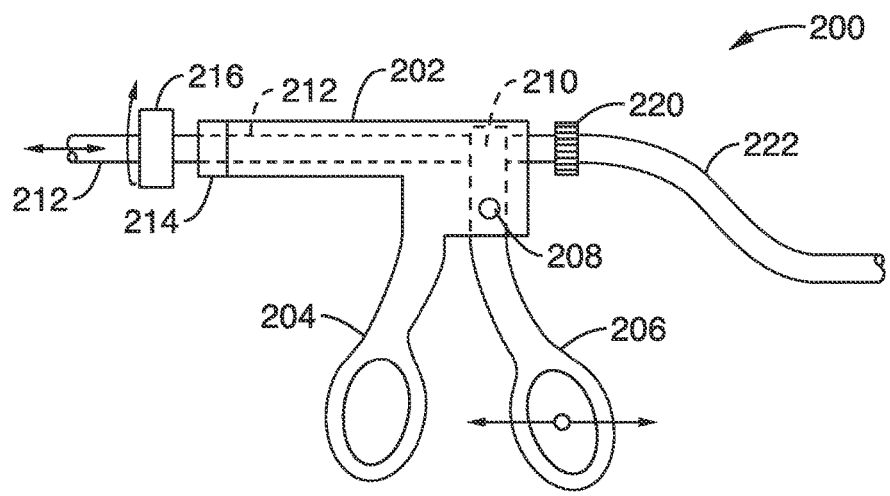
FIG. 12 is a side view of an alternative pistol grip with handle rotation adjust dial that may be used with the device of FIG. 1.

FIG. 12 illustrates an alternative proximal handle 200 having a pistol grip lever 206 that rotates about pin 208 with respect to stationary handle 204 to drive axial motion of inner shaft 212 at lever 210. Stationary handle 204 and lever body 202 act as the main handle body, and lever 210 acts as the secondary handle body to drive motion of the inner shaft 212.

FIG. 12 also shows a rotation adjustment dial 216 configuration that may be used with any of the proximal handles described herein. The orientation adjustment dial or knob 216 that allows the user to control the orientation of the bipolar tips 12*a* and 12*b* separately from rotating their wrist. To change the attitude of the distal forceps jaws 12*a* and 12*b*, the dial or knob 216 is rotated to the desired angle with respect to the collet nut 214 on lever body 202, correspondingly rotating the inner shaft 50 about the longitudinal axis. Such configuration is especially useful when using the angled forceps jaws 14*c* of FIG. 8. The benefit of orientation control independent of wrist rotation is also important for the straight 14*b* and tapered 14*a* tip geometries. Benefits include improved ergonomics and line of sight.

For electrosurgical applications, wiring 222 (e.g. for bipolar leads) may be attached to the handle 200 (or handles 60, 250) via connector 220.

Figure 13:
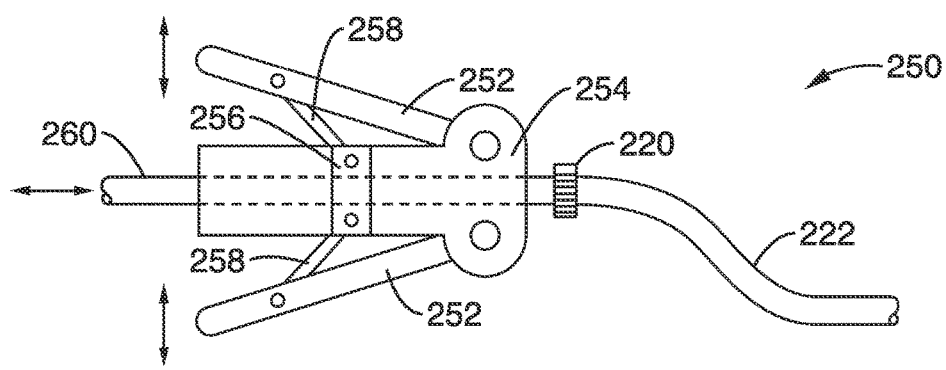
FIG. 13 is a side view of an alternative tweezers handle configuration that may be used with the device of FIG. 1.

FIG. 13 illustrates a reverse tweezers-type handle assembly 250. Handle ends 252 may be pivotably coupled to body 254 to drive actuation member 256 via connectors 258. This, in turn, drives the axial motion of the inner shaft 260.

It is appreciated that the type of handle (e.g. handle assemblies 60, 200, and 250) selected is arbitrary; with the only requirement being that the handle is able to translate the inner shaft back and forth along the axial direction.

It is sometimes convenient to use irrigation to wash away debris from the target treatment site being cauterized or dissected. In one configuration (not shown), the hollow inner shaft 50 (see FIG. 3) may be used to incorporate the ability to flow irrigation solution through the shaft 50 and out of the tip 12*a*, 12*b* location through the implementation of a delivery channel (not shown) inside the actuating member 42 and handle transition 80. The ability for the micro-bipolar cautery device 10 to administer irrigation solution eliminates the need for an additional medical device. The activation of the irrigation is usually controlled by a foot pedal and corresponding pumping system (both not shown).

Since a primary target function of device 10 is bipolar cauterization, tips 12*a* and 12*b* preferably acts as bipolar electrodes, with wiring 222 running along the length of the device 10 from proximal end 61 to the distal end 21. Leads 222 (shown in FIGS. 12 and 13) may be fed through the inner shaft 50, or between inner shaft 50 and outer sheath 88.

In a preferred embodiment, two bipolar tips 12*a* and 12*b* are electrically isolated and act as the electrical charge carriers (e.g. bipolar electrodes). Accordingly, electrical isolation is very important to operation. To electrically isolate the bipolar tips 12*a* and 12*b*, non-conductive materials (such as HDPE, ABS, or other suitable plastic material) may be used for the dovetail coupling 30 and/or actuating member 42.

In an alternative embodiment (not shown), electrodes (not shown) may be bonded or welded to the two tips 12*a* and 12*b*. In a preferred embodiment, one or more of tips 12*a* and 12*b*, dovetail coupling 30, and actuating member 42 may have some sort of non-stick coating applied. The suggested coating should be of Teflon, Polytetrafluoroethylene (PTFE), or similar composition.

In a preferred embodiment, non-insulating parts were made of medical grade stainless steel, and manufactured with use of EDM machinery available in the art. For example, one or more of the tips 12*a*, 12*b*, coupling 30, and actuating member 42 may be machined using wire EDM, die-sinker type EDM, or a 3-axis CNC machine.

It is also appreciated that the micro-endoscopic device 10 of the technology described herein may be used for applications, not involving electrosurgery (or cauterizing) where application of a finite gripper or dissection device are needed.

FIG. 1 through FIG. 13 are described and detailed above for specific use in neurosurgical endoscopic procedures. However, it is appreciated that the devices shown in FIG. 1 through FIG. 13, with or without modification, are directly applicable to other minimally invasive surgical procedures, such as, without limitation, procedures such as laparoscopy, thorascopy, etc.

A particular advantage of the device 10 of the technology described herein is parallel tip 12*a*, 12*b* motion, which is using dovetails to constrain the motion of the tips vertically. This keeps the distance to the tissue constant when closing and opening, and allows the surgeon more accurate control. Also, the parallel motion of the tips allows the device to be used for micro-dissection.

The device 10 of the technology described herein provides significant improvement over presently available devices, which typically use a tweezers-style motion to close the tips, typically achieved by cylindrical shafts and rods that slide relative to each other to compress the two forceps. This allows the tips to move axially and changes the distance between the tips and the tissue as the device is closing and opening, and makes the device more difficult to use and less accurate when cauterizing tissue. Also, a tweezers-style device cannot be used for spreading tissue since the maximum distance between the forceps is limited and angled in a "v" shape.

The parallel tip motion of the device 10 of the technology described herein allows the entire tip to move and be spread apart, which allows the surgeon more surface area to use to spread the tissue and a wider range of motion.

From the discussion above it will be appreciated that the technology described herein can be embodied in various ways, including the following:

1. An endoscopic electrosurgical forceps apparatus, comprising: a proximal handle assembly comprising at least one actuating handle; an outer tube having a longitudinal axis and a proximal end coupled to and extending from said proximal handle assembly; an inner shaft slidably disposed in said outer tube, said inner shaft having a proximal end coupled to the proximal handle assembly; wherein the inner shaft and outer tube are coupled to the proximal handle assembly such that actuation of the at least one actuating handle drives the inner shaft to translate axially within the outer tube along the longitudinal axis; a pair of forceps tips each having a free distal end and a proximal end coupled to the inner shaft via an actuating member; and a coupling member coupled to the actuating member and forceps tips; said forceps tips being slidably coupled to said coupling member such that axial motion of the inner shaft within the outer tube as a result of operation of said proximal handle assembly drives the forceps tips to open and close with respect to each other; wherein motion of the forceps tips from an open orientation to a closed orientation is substantially orthogonal to the longitudinal axis such that the distal ends of the forceps tips are constrained at the same axial location along the longitudinal axis.

2. The apparatus of any preceding embodiment: wherein the forceps tips each have a gripping surface extending toward the distal end of the forceps tips; and wherein gripping surfaces of respective forceps tips are configured to be substantially parallel to each other throughout translation of the forceps from the closed orientation to the open orientation and from the open orientation to the closed orientation.

3. The apparatus of any preceding embodiment, wherein the forceps tips comprise bipolar electrosurgical electrodes configured to cauterize tissue in contact with the forceps tips.

4. The apparatus of any preceding embodiment: wherein the forceps tips each form individual bipolar electrodes; and wherein the coupling member is constructed of an insulating material to electrically isolate the forceps tips from each other.

5. The apparatus of any preceding embodiment: wherein each of the forceps tips form a dovetail joint with respect to the coupling member; and wherein the dovetail joint constrains motion of the forceps tips orthogonally to the longitudinal axis.

6. The apparatus of any preceding embodiment: wherein the actuating member is fixed to the distal end of the inner shaft; wherein the coupling member is fixed to the outer shaft; and wherein the actuating member is configured to slideably reciprocate within an axial channel of the coupling member to drive actuation of the forceps tips.

7. The apparatus of any preceding embodiment: wherein the actuating member comprises one or more drive slots; wherein each of the forceps tips comprise a drive pin configured to be received in the one or more drive slots; and wherein axial motion of the inner shaft drives motion of the pins within said slots to affect translation of the forceps tips along the dovetail joint in a substantially orthogonal direction with respect to the longitudinal axis.

8. The apparatus of any preceding embodiment, wherein the one or more drive slots are oriented at an angle with respect to the longitudinal axis.

9. The apparatus of any preceding embodiment: wherein said handle assembly comprises a main handle body and a secondary handle body; wherein the inner shaft is fixed to the secondary handle body and the outer tube is fixed to the main handle body; and wherein actuation of said handle affect motion with respect to the main handle body and the secondary handle body to drive the inner shaft to translate axially within the outer tube along the longitudinal axis.

10. The apparatus of any preceding embodiment: wherein the at least one actuating handle comprises first and second actuating handles; and wherein the first and second actuating handles are pivotably connected to main handle body and the secondary handle body to allow a tweezers-like motion of the first and second actuating handles to affect motion with respect to the main handle body and the secondary handle body.

11. An endoscopic electrosurgical apparatus, comprising: a proximal handle assembly comprising at least one actuating handle; an outer tube having a longitudinal axis and a proximal end coupled to and extending from said proximal handle assembly; an inner shaft slidably disposed in said outer tube, said inner shaft having a proximal end coupled to the proximal handle assembly; wherein the inner shaft and outer tube are coupled to the proximal handle assembly such that actuation of the at least one actuating handle drives the inner shaft to translate axially within the outer tube along the longitudinal axis; a pair of moveable tips each having a free distal end and a proximal end coupled to the inner shaft via an actuating member; wherein the moveable tips comprise bipolar electrosurgical electrodes configured to cauterize tissue in contact with the moveable tips; and a coupling member coupled to the actuating member and moveable tips; said moveable tips being slidably coupled to said coupling member such that axial motion of the inner shaft within the outer tube as a result of operation of said proximal handle assembly drives the moveable tips to open and close with respect to each other; wherein motion of the moveable tips from an open orientation to a closed orientation is substantially orthogonal to the longitudinal axis such that the distal ends of the moveable tips are constrained at the same axial location along the longitudinal axis.

12. The apparatus of any preceding embodiment: wherein the moveable tips each have a gripping surface extending toward the distal end of the moveable tips; and wherein gripping surfaces of respective moveable tips are configured to be substantially parallel to each other throughout translation of the moveable from the closed orientation to the open orientation and from the open orientation to the closed orientation.

13. The apparatus of any preceding embodiment, wherein the moveable tips comprise forceps tips.

14. The apparatus of any preceding embodiment: wherein the moveable tips each form individual bipolar electrodes; and wherein the coupling member is constructed of an insulating material to electrically isolate the moveable tips from each other.

15. The apparatus of any preceding embodiment: wherein each of the moveable tips form a dovetail joint with respect to the coupling member; wherein the dovetail joint constrains motion of the moveable tips orthogonally to the longitudinal axis.

16. The apparatus of any preceding embodiment: wherein the actuating member is fixed to the distal end of the inner shaft; wherein the coupling member is fixed to the outer shaft; and wherein the actuating member is configured to slideably reciprocate within an axial channel of the coupling member to drive actuation of the moveable tips.

17. The apparatus of any preceding embodiment: wherein the actuating member comprises one or more drive slots; wherein each of the moveable tips comprise a drive pin configured to be received in the one or more drive slots; and wherein axial motion of the inner shaft drives motion of the pins within said slots to affect translation of the moveable tips along the dovetail joint in a substantially orthogonal direction with respect to the longitudinal axis.

18. The apparatus of any preceding embodiment, wherein the one or more drive slots are oriented at an angle with respect to the longitudinal axis.

19. The apparatus of any preceding embodiment: wherein said handle assembly comprises a main handle body and a secondary handle body; wherein the inner shaft is fixed to the secondary handle body and the outer tube is fixed to the main handle body; and wherein actuation of said handle affect motion with respect to the main handle body and the secondary handle body to drive the inner shaft to translate axially within the outer tube along the longitudinal axis.

20. The apparatus of any preceding embodiment: wherein the at least one actuating handle comprises first and second actuating handles; and wherein the first and second actuating handles are pivotably connected to main handle body and the secondary handle body the to allow a tweezers-like motion of the first and second actuating handles to affect motion with respect to the main handle body and the secondary handle body.

21. An endoscopic electrosurgical forceps apparatus, comprising: a proximal handle assembly comprising at least one actuating handle; an outer tube having a longitudinal axis and a proximal end coupled to and extending from said proximal handle assembly; an inner shaft slidably disposed in said outer tube, said inner shaft having a proximal end coupled to the proximal handle assembly; wherein the inner shaft and outer tube are coupled to the proximal handle assembly such that actuation of the at least one actuating handle drives the inner shaft to translate axially within the outer tube along the longitudinal axis; a pair of forceps tips each having a free distal end and a proximal end coupled to the inner shaft via an actuating member; wherein the forceps tips comprise bipolar electrosurgical electrodes configured to cauterize tissue in contact with the forceps tips; and a coupling member coupled to the actuating member and forceps tips; said forceps tips forming at least one dovetail joint with said coupling member such that axial motion of the inner shaft within the outer tube as a result of operation of said proximal handle assembly drives the forceps tips to open and close with respect to each other; wherein the at least one dovetail joint allows sliding motion of the forceps with respect to the dovetail coupling member such that the motion of the forceps tips from an open orientation to a closed orientation is substantially orthogonal to the longitudinal axis such that the distal ends of the forceps tips are constrained at the same axial location along the longitudinal axis.

22. The apparatus of any preceding embodiment: wherein the forceps tips each have a gripping surface extending toward the distal end of the forceps tips; and wherein gripping surfaces of respective forceps tips are configured to be substantially parallel to each other throughout translation of the forceps from the closed orientation to the open orientation and from the open orientation to the closed orientation.

23. The apparatus of any preceding embodiment: wherein the forceps tips each form individual bipolar electrodes; and wherein the coupling member is constructed of an insulating material to electrically isolate the forceps tips from each other.

24. The apparatus of any preceding embodiment: wherein the actuating member is fixed to the distal end of the inner shaft; wherein the coupling member is fixed to the outer shaft; and wherein the actuating member is configured to slideably reciprocate within an axial channel of the coupling member to drive actuation of the forceps tips.

25. The apparatus of any preceding embodiment: wherein the actuating member comprises one or more drive slots; wherein each of the forceps tips comprise a drive pin configured to be received in the one or more drive slots; and wherein axial motion of the inner shaft drives motion of the pins within said slots to affect translation of the forceps tips along the dovetail joint in a substantially orthogonal direction with respect to the longitudinal axis.

26. The apparatus of any preceding embodiment, wherein the one or more drive slots are oriented at an angle with respect to the longitudinal axis.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step plus function" element unless the element is expressly recited using the phrase "step for".

What is claimed is:

1. An endoscopic electrosurgical forceps apparatus, comprising:
a proximal handle assembly comprising at least one actuating handle;
an outer tube having a longitudinal axis and a proximal end coupled to and extending from said proximal handle assembly;
an inner shaft slidably disposed in said outer tube, said inner shaft having a proximal end coupled to the proximal handle assembly;
wherein the inner shaft and outer tube are coupled to the proximal handle assembly such that actuation of the at least one actuating handle drives the inner shaft to translate axially within the outer tube along the longitudinal axis;
a pair of forceps tips each having a free distal end and a proximal end coupled to the inner shaft via an actuating member; and
a coupling member coupled to the actuating member and forceps tips;
said forceps tips being slidably coupled to said coupling member such that axial motion of the inner shaft within the outer tube as a result of operation of said proximal handle assembly drives the forceps tips to open and close with respect to each other;
wherein motion of the forceps tips from an open orientation to a closed orientation is substantially orthogonal to the longitudinal axis such that the distal ends of the forceps tips are constrained at the same axial location along the longitudinal axis;
wherein the forceps tips comprise bipolar electrosurgical electrodes configured to cauterize tissue in contact with the forceps tips;
wherein each of the forceps tips form a dovetail joint with respect to the coupling member;
wherein the dovetail joint constrains motion of the forceps tips orthogonally to the longitudinal axis;
wherein the actuating member is fixed to a distal end of the inner shaft;

wherein the coupling member is fixed to the outer tube; and wherein the actuating member is configured to slideably reciprocate within an axial channel of the coupling member to drive actuation of the forceps tips.

2. An apparatus as recited in claim 1:

wherein the forceps tips each have a gripping surface extending toward the distal end of the forceps tips; and wherein gripping surfaces of respective forceps tips are configured to be substantially parallel to each other throughout translation of the forceps tips from the closed orientation to the open orientation and from the open orientation to the closed orientation.

3. An apparatus as recited in claim 1:

wherein the forceps tips each form individual bipolar electrodes; and wherein the coupling member is constructed of an insulating material to electrically isolate the forceps tips from each other.

4. An apparatus as recited in claim 1:

wherein the actuating member comprises one or more drive slots;

wherein each of the forceps tips comprises a drive pin configured to be received in the one or more drive slots; and wherein axial motion of the inner shaft drives motion of the pins within said slots to affect translation of the forceps tips along the dovetail joint in a substantially orthogonal direction with respect to the longitudinal axis.

5. An apparatus as recited in claim 4, wherein the one or more drive slots are oriented at an angle with respect to the longitudinal axis.

6. An apparatus as recited in claim 1:

wherein said handle assembly comprises a main handle body and a secondary handle body;

wherein the inner shaft is fixed to the secondary handle body and the outer tube is fixed to the main handle body; and wherein actuation of said handle assembly affects motion with respect to the main handle body and the secondary handle body to drive the inner shaft to translate axially within the outer tube along the longitudinal axis.

7. An apparatus as recited in claim 6:

wherein the at least one actuating handle comprises first and second actuating handles; and wherein the first and second actuating handles are pivotably connected to the main handle body and the secondary handle body to allow a tweezers-like motion of the first and second actuating handles to affect motion with respect to the main handle body and the secondary handle body.

8. An endoscopic electrosurgical apparatus, comprising:

a proximal handle assembly comprising at least one actuating handle;

an outer tube having a longitudinal axis and a proximal end coupled to and extending from said proximal handle assembly;

an inner shaft slidably disposed in said outer tube, said inner shaft having a proximal end coupled to the proximal handle assembly;

wherein the inner shaft and outer tube are coupled to the proximal handle assembly such that actuation of the at least one actuating handle drives the inner shaft to translate axially within the outer tube along the longitudinal axis;

a pair of moveable tips each having a free distal end and a proximal end coupled to the inner shaft via an actuating member;

wherein the moveable tips comprise bipolar electrosurgical electrodes configured to cauterize tissue in contact with the moveable tips; and a coupling member coupled to the actuating member and moveable tips;

said moveable tips being slidably coupled to said coupling member such that axial motion of the inner shaft within the outer tube as a result of operation of said proximal handle assembly drives the moveable tips to open and close with respect to each other;

wherein motion of the moveable tips from an open orientation to a closed orientation is substantially orthogonal to the longitudinal axis such that the distal ends of the moveable tips are constrained at the same axial location along the longitudinal axis;

wherein each of the moveable tips form a dovetail joint with respect to the coupling member;

wherein the dovetail joint constrains motion of the moveable tips orthogonally to the longitudinal axis;

wherein the actuating member is fixed to a distal end of the inner shaft;

wherein the coupling member is fixed to the outer tube; and wherein the actuating member is configured to slideably reciprocate within an axial channel of the coupling member to drive actuation of the moveable tips.

9. An apparatus as recited in claim 8:

wherein the moveable tips each have a gripping surface extending toward the distal end of the moveable tips; and wherein gripping surfaces of respective moveable tips are configured to be substantially parallel to each other throughout translation of the moveable tips from the closed orientation to the open orientation and from the open orientation to the closed orientation.

10. An apparatus as recited in claim 8, wherein the moveable tips comprise forceps tips.

11. An apparatus as recited in claim 8:

wherein the moveable tips each form individual bipolar electrodes; and wherein the coupling member is constructed of an insulating material to electrically isolate the moveable tips from each other.

12. An apparatus as recited in claim 8:

wherein the actuating member comprises one or more drive slots;

wherein each of the moveable tips comprises a drive pin configured to be received in the one or more drive slots; and wherein axial motion of the inner shaft drives motion of the pins within said slots to affect translation of the moveable tips along the dovetail joint in a substantially orthogonal direction with respect to the longitudinal axis.

13. An apparatus as recited in claim 12, wherein the one or more drive slots are oriented at an angle with respect to the longitudinal axis.

14. An apparatus as recited in claim 8:

wherein said handle assembly comprises a main handle body and a secondary handle body;

wherein the inner shaft is fixed to the secondary handle body and the outer tube is fixed to the main handle body; and wherein actuation of said handle assembly affects motion with respect to the main handle body and the secondary handle body to drive the inner shaft to translate axially within the outer tube along the longitudinal axis.

15. An apparatus as recited in claim 14:
   wherein the at least one actuating handle comprises first and second actuating handles; and
   wherein the first and second actuating handles are pivotably connected to the main handle body and the secondary handle body the to allow a tweezers-like motion of the first and second actuating handles to affect motion with respect to the main handle body and the secondary handle body.

16. An endoscopic electrosurgical forceps apparatus, comprising:
   a proximal handle assembly comprising at least one actuating handle;
   an outer tube having a longitudinal axis and a proximal end coupled to and extending from said proximal handle assembly;
   an inner shaft slidably disposed in said outer tube, said inner shaft having a proximal end coupled to the proximal handle assembly;
   wherein the inner shaft and outer tube are coupled to the proximal handle assembly such that actuation of the at least one actuating handle drives the inner shaft to translate axially within the outer tube along the longitudinal axis;
   a pair of forceps tips each having a free distal end and a proximal end coupled to the inner shaft via an actuating member;
   wherein the forceps tips comprise bipolar electrosurgical electrodes configured to cauterize tissue in contact with the forceps tips; and
   a coupling member coupled to the actuating member and forceps tips;
   said forceps tips forming at least one dovetail joint with said coupling member such that axial motion of the inner shaft within the outer tube as a result of operation of said proximal handle assembly drives the forceps tips to open and close with respect to each other;
   wherein the at least one dovetail joint allows sliding motion of the forceps tips with respect to the coupling member such that the motion of the forceps tips from an open orientation to a closed orientation is substantially orthogonal to the longitudinal axis such that the distal ends of the forceps tips are constrained at the same axial location along the longitudinal axis;
   wherein the actuating member is fixed to a distal end of the inner shaft;
   wherein the coupling member is fixed to the outer tube; and
   wherein the actuating member is configured to slideably reciprocate within an axial channel of the coupling member to drive actuation of the forceps tips.

17. An apparatus as recited in claim 16:
   wherein the forceps tips each have a gripping surface extending toward the distal end of the forceps tips; and
   wherein gripping surfaces of respective forceps tips are configured to be substantially parallel to each other throughout translation of the forceps tips from the closed orientation to the open orientation and from the open orientation to the closed orientation.

18. An apparatus as recited in claim 16:
   wherein the forceps tips each form individual bipolar electrodes; and
   wherein the coupling member is constructed of an insulating material to electrically isolate the forceps tips from each other.

19. An apparatus as recited in claim 16:
   wherein the actuating member comprises one or more drive slots;
   wherein each of the forceps tips comprises a drive pin configured to be received in the one or more drive slots; and
   wherein axial motion of the inner shaft drives motion of the pins within said slots to affect translation of the forceps tips along the dovetail joint in a substantially orthogonal direction with respect to the longitudinal axis.

20. An apparatus as recited in claim 19, wherein the one or more drive slots are oriented at an angle with respect to the longitudinal axis.

* * * * *